United States Patent
Yang et al.

(10) Patent No.: US 12,049,524 B2
(45) Date of Patent: Jul. 30, 2024

(54) IODINE COMPLEX AND PREPARATION METHOD THEREFOR AND USE THEREOF

(71) Applicant: NOVASHIN CO., LTD., Beijing (CN)

(72) Inventors: Jianchun Yang, Beijing (CN); Dongmei Yang, Beijing (CN); Chengqiang Yan, Beijing (CN); Rongxin Zhu, Beijing (CN); Fan Wang, Beijing (CN)

(73) Assignee: NOVASHIN CO., LTD., Beijing (CN)

( * ) Notice: Subject to any disclaimer, the term of this patent is extended or adjusted under 35 U.S.C. 154(b) by 783 days.

(21) Appl. No.: 17/263,145

(22) PCT Filed: Mar. 11, 2020

(86) PCT No.: PCT/CN2020/078730
§ 371 (c)(1),
(2) Date: Jan. 25, 2021

(87) PCT Pub. No.: WO2020/199872
PCT Pub. Date: Oct. 8, 2020

(65) Prior Publication Data
US 2021/0292443 A1    Sep. 23, 2021

(30) Foreign Application Priority Data

Apr. 2, 2019    (CN) .......................... 201910263342.5

(51) Int. Cl.
*C08F 8/08*         (2006.01)
*C08C 19/06*        (2006.01)
(Continued)

(52) U.S. Cl.
CPC .............. *C08C 19/14* (2013.01); *C08C 19/06* (2013.01); *C08J 5/18* (2013.01); *C08J 7/12* (2013.01);
(Continued)

(58) Field of Classification Search
CPC ....... A61K 31/79; A61K 2300/00; C08F 8/08; C08F 36/06; C08F 136/06; C08F 236/06
See application file for complete search history.

(56) References Cited

U.S. PATENT DOCUMENTS

| 8,520,171 B2 | 8/2013 | Kitagawa et al. |
| 9,645,292 B2 | 5/2017 | Goto et al. |

(Continued)

FOREIGN PATENT DOCUMENTS

| CN | 85106262 A | 2/1987 |
| CN | 102002132 A | 4/2011 |

(Continued)

OTHER PUBLICATIONS

Marvel et al. The Structure of Vinyl Polymers. II.1 Polyvinyl Alcohol. Journal of the American Chemical Society 1938, 60, 1045-1051 (Year: 1938).*

(Continued)

*Primary Examiner* — Mark S Kaucher
(74) *Attorney, Agent, or Firm* — NKL Law; Allen Xue

(57) ABSTRACT

An iodine complex is formed by complexing a unit having a structure as represented by formula (I) with iodine molecules or iodine molecules with polyiodide ions formed by combining iodine ions. As a carrier, a polymer is complexed with iodine to obtain an iodine complex for formula (I).

(Continued)

-continued

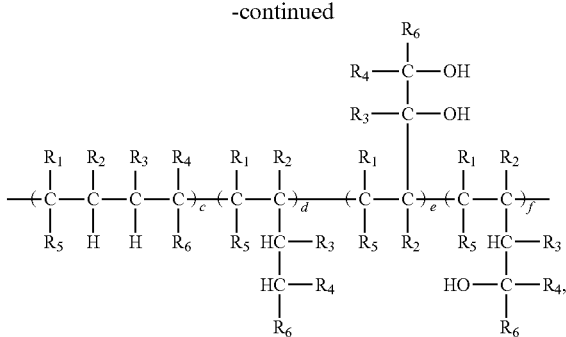

The iodine complex can be used as a radioactive marker, or used in an iodine therapeutic agent, or used in a polarizer. The polymer carrier has good biocompatibility. The content of iodine complex can be adjusted according to requirements, and the content of the iodine can be adjusted within a range of 0.001-60%. The difference in the content of the iodine can affect the transmission clarity of the iodine complex as a radiographic marker.

20 Claims, 2 Drawing Sheets

(51) Int. Cl.
  *C08C 19/14* (2006.01)
  *C08J 5/18* (2006.01)
  *C08J 7/12* (2006.01)
  *G02B 1/04* (2006.01)
  *G02B 5/30* (2006.01)

(52) U.S. Cl.
  CPC ........... *G02B 1/041* (2013.01); *G02B 5/3033* (2013.01); *C08J 2315/00* (2013.01)

(56) References Cited

U.S. PATENT DOCUMENTS

| | | |
|---|---|---|
| 2011/0315306 A1 | 12/2011 | Goto et al. |
| 2012/0055621 A1 | 3/2012 | Goto et al. |
| 2012/0056211 A1 | 3/2012 | Kitagawa et al. |
| 2012/0057104 A1 | 3/2012 | Kitagawa et al. |
| 2012/0057107 A1 | 3/2012 | Kitagawa et al. |
| 2012/0057231 A1 | 3/2012 | Goto et al. |
| 2012/0057232 A1 | 3/2012 | Goto et al. |
| 2012/0058321 A1 | 3/2012 | Goto et al. |
| 2012/0327512 A1 | 12/2012 | Goto et al. |
| 2013/0100529 A1 | 4/2013 | Kitagawa et al. |

FOREIGN PATENT DOCUMENTS

| | | |
|---|---|---|
| CN | 103374127 A | 10/2013 |
| CN | 104955856 A | 9/2015 |

OTHER PUBLICATIONS

Kikukawa et al. Polymer Journal 1971, vol. 2, No. 2, 212-219 (Year: 1971).*

* cited by examiner

IODINE COMPLEX AND PREPARATION METHOD THEREFOR AND USE THEREOF

CROSS-REFERENCE TO RELATED APPLICATIONS

The present application is national entry of International Application No. PCT/CN2020/078730 filed on Mar. 11, 2020, which claims the benefit of priority to the prior application No. 201910263342.5 submitted to China National Intellectual Property Administration on Apr. 2, 2019 which is entitled "An iodine complex and its preparation method and application thereof", the entire contents of the prior application are incorporated herein by reference.

FIELD OF THE INVENTION

The present invention belongs to the technical field of iodine complex, in particularly relates to an iodine complex and its preparation method and the use as radiation marker, or the use in iodine therapeutics, or in polarizing film.

BACKGROUND OF THE INVENTION

Iodine is one of the most important elements for animals and plants, it is an essential trace element for human body. Iodine can complex with many substances, such as amino acids and polyvinylpyrrolidone (PVP). The complexes obtained are soluble in water, commonly used as plant nutrients, disinfectants, etc.; however, due to the complexes of obtained by complexing these substances with iodine are easily soluble in water and/or alcohol, their application range is limited.

In nature, the complex formed by starch and iodine exhibits the maximum absorption at 620-680 nm, shows a colour of dark blue; therefore many chemical titration techniques based on iodine use starch as an indicator. Amylose may swell and be dissolved in water, but the spiral structures formed by the effects of the hydrogen bonds of the hydroxyl groups on glucose are destroyed, the ability of starch in dissolved state to bind iodine drops sharply.

Iodine and iodine compounds are the main components of the contrast agents due to their radiopacity. Radioactive compounds prepared by introducing radioactive iodine[131], iodine[125] and iodine[123] etc. into the compound carriers may be applied to protein iodination labeling. However, the binding capacity of the existing compound carriers is limited, the amount of iodine bound is limited. Therefore, searching for a suitable compound carrier has always been one of the researches and development focuses in these application fields.

In polyvinyl alcohol (PVA) membrane stretched after being dyed with iodine, iodine molecules are aligned on the PVA membrane, and can form a polarizing membrane with uniform bidirectional absorption. PVA is obtained by hydrolysis of vinyl acetate polymer; during the production process, the degree of polymerization, the degree of hydrolysis of ester groups, and the configuration of the polymer affect the binding capacity of PVA to iodine; PVA has high water solubility, but it has weak ability to bind iodine molecules; PVA iodine membrane will suffer iodine loss when being heated. How to improve the durability of PVA iodine membrane in high temperature and high humidity environment has always been the technical difficulty and research hotspot of polarizers.

SUMMERY OF THE INVENTION

In order to improve the deficiencies of the prior arts, the object of the present invention is to provide an iodine complex and its preparation method and application thereof, the iodine complex can be used as a radiation marker (such as a radiopaque marker), it can also be used to prepare iodine therapeutics, and to prepare polarizers; the iodine complex is formed by complexing the polymer carrier and iodine, the polymer carrier has good biocompatibility. The content of iodine in the iodine complex can be adjusted as needed, for example, a mass content of iodine is adjustable within 0.001-60 wt %.

The object of the present invention is achieved by the following technical solutions:

The present invention provides a use of a polymer comprising a structural unit represented by Formula (I) and optionally at least one of structural units represented by Formula (II), Formula (III) and Formula (IV) as iodine carrier, the use comprises:

complexing the polymer comprising a structural unit represented by Formula (I) and optionally at least one of structural units represented by Formula (II), Formula (III) and Formula (IV) as a carrier with iodine, to get the iodine complex:

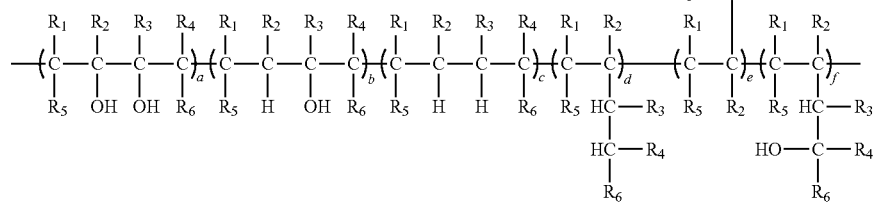

Formula (I)

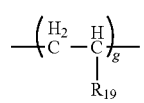

Formula (II)

-continued

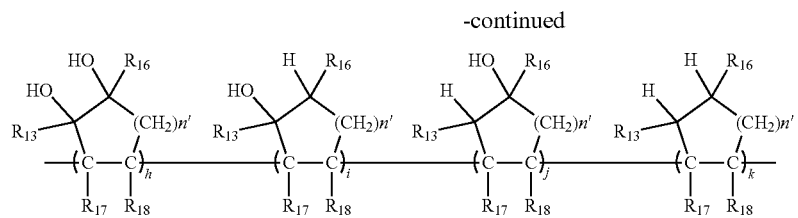

Formula (III)

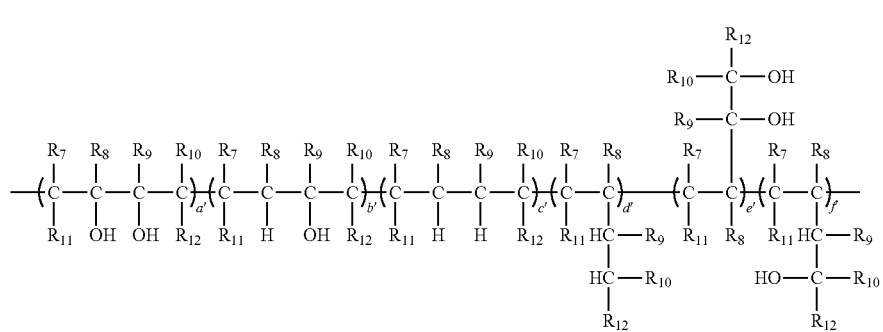

Formula (IV)

in Formula (I), $R_1$, $R_2$, $R_3$, $R_4$, $R_5$ and $R_6$ are the same or different, independently selected from H, $C_{1-8}$ alkyl, $C_{6-20}$ aryl that is unsubstituted or optionally substituted with one, two or more $R_a$; each $R_a$ is the same or different, independently selected from $C_{1-12}$ alkyl;

a, b, c, d, e and f are independently integers greater than or equal to 0, and a and e are not 0 at the same time;

in Formula (II), $R_{19}$ is selected from H, cyano, $C_{1-8}$ alkyl, the following groups that are unsubstituted or optionally substituted with one, two or more $R_a$: $C_{3-10}$ cycloalkyl, $C_{6-20}$ aryl; each $R_a$ is the same or different, independently selected from $C_{1-12}$ alkyl;

g is an integer greater than or equal to 1;

in Formula (III), $R_{13}$, $R_{16}$, $R_{17}$ and $R_{18}$ are the same or different, independently selected from H, $C_{1-8}$ alkyl, $C_{6-20}$ aryl that is unsubstituted or optionally substituted with one, two or more $R_a$; each $R_a$ is the same or different, independently selected from $C_{1-12}$ alkyl;

h, i, j, k and n' are independently integers greater than or equal to 1;

in Formula (IV), $R_7$, $R_8$, $R_9$, $R_{10}$, $R_{11}$ and $R_{12}$ are the same or different, independently selected from H, $C_{1-8}$ alkyl, $C_{6-20}$ aryl that is unsubstituted or optionally substituted with one, two or more $R_a$; each $R_a$ is the same or different, independently selected from $C_{1-12}$ alkyl;

a', b', c', d', e' and f' are independently integers greater than or equal to 0, and are not 0 at the same time.

The present invention also provides an iodine complex, wherein the iodine complex is an iodine compound obtained by complexing a polymer comprising a structural unit represented by Formula (I) and optionally at least one of the structural units represented by Formula (II), Formula (III) and Formula (IV) as a carrier with iodine:

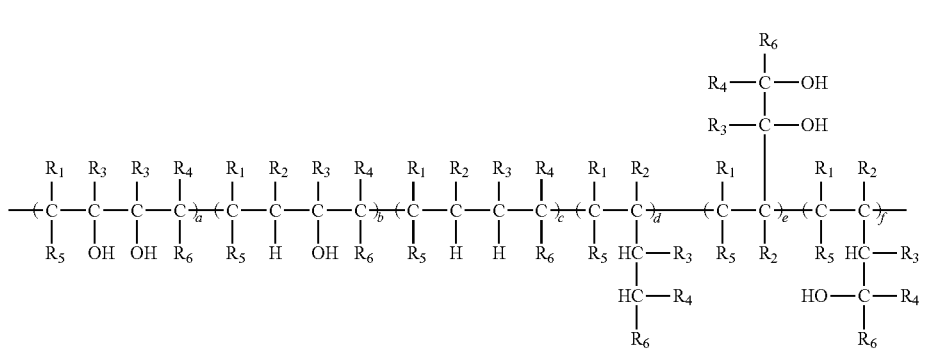

Formula (I)

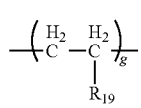

Formula (II)

-continued

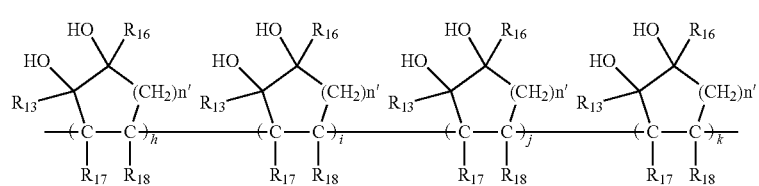

Formula (III)

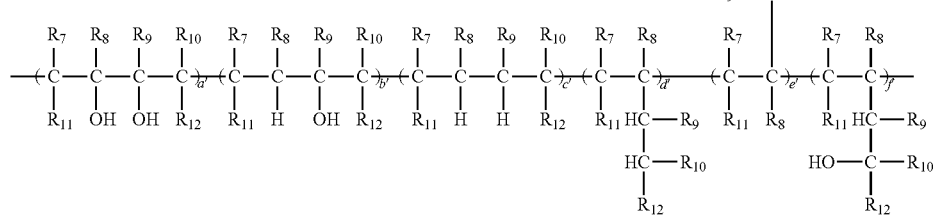

Formula (IV)

in Formula (I), $R_1$, $R_2$, $R_3$, $R_4$, $R_5$ and $R_6$ are the same or different, independently selected from H, $C_{1-8}$ alkyl, $C_{6-20}$ aryl that is unsubstituted or optionally substituted with one, two or more $R_a$; each $R_a$ is the same or different, independently selected from $C_{1-12}$ alkyl;

a, b, c, d, e and f are independently integers greater than or equal to 0, and a and e are not 0 at the same time;

in Formula (II), $R_{19}$ is selected from H, cyano, $C_{1-8}$ alkyl, the following groups that are unsubstituted or optionally substituted with one, two or more $R_a$: $C_{3-10}$ cycloalkyl, $C_{6-20}$ aryl; each $R_a$ is the same or different, independently selected from $C_{1-12}$ alkyl;

g is an integer greater than or equal to 1;

in Formula (III), $R_{13}$, $R_{16}$, $R_{17}$ and $R_{18}$ are the same or different, independently selected from H, $C_{1-8}$ alkyl, $C_{6-20}$ aryl that is unsubstituted or optionally substituted with one, two or more $R_a$; each $R_a$ is the same or different, independently selected from $C_{1-12}$ alkyl;

h, i, j, k and n' are independently integers greater than or equal to 1;

in Formula (IV), $R_7$, $R_8$, $R_9$, $R_{10}$, $R_{11}$ and $R_{12}$ are the same or different, independently selected from H, $C_{1-8}$ alkyl, $C_{6-20}$ aryl that is unsubstituted or optionally substituted with one, two or more $R_a$; each $R_a$ is the same or different, independently selected from $C_{1-12}$ alkyl;

a', b', c', d', e' and f' are independently integers greater than or equal to 0, and are not 0 at the same time.

According to the present invention, the complexing refers to binding the iodine with the polymer molecules through, including but not being limited to, coordination bonds and/or van der Waals force, etc. Exemplarily, the polymer forms a complex by coordination between the lone pairs of electrons provided by oxygen atoms in two pairs of the adjacent hydroxyl groups and the vacant orbitals provided by the iodine; for example, the following binding manner may be adopted:

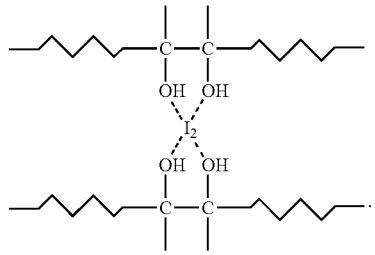

According to the present invention, the iodine is one of an iodine molecule, and a polyiodide formed by binding an iodine molecule with an iodide ion, or a mixture of them.

According to the present invention, the polymer may be a homopolymer, and may also be a random copolymer or a block copolymer.

According to the present invention, $R_1$, $R_2$, $R_3$, $R_4$, $R_5$ and $R_6$ are the same or different, independently selected from H, $C_{1-4}$ alkyl, $C_{6-10}$ aryl that is unsubstituted or optionally substituted by one, two or more $R_a$; $R_a$ is as defined above. Preferably, $R_1$, $R_2$, $R_3$, $R_4$, $R_5$ and $R_6$ are the same or different, independently selected from H, methyl, phenyl, tolyl. Further preferably, $R_1$, $R_2$, $R_3$, $R_4$, $R_5$ and $R_6$ are the same or different, independently selected from H, methyl. Further preferably, $R_1$, $R_2$, $R_3$, $R_4$, $R_5$ and $R_6$ are the same, selected from H.

According to the present invention, $R_{19}$ is selected from H, cyano, $C_{1-4}$ alkyl, $C_{6-10}$ aryl that is unsubstituted or optionally substituted by one, two or more $R_a$; $R_a$ is as defined above. Preferably, $R_{19}$ is selected from phenyl, tolyl, cyano.

According to the present invention, $R_7$, $R_8$, $R_9$, $R_{10}$, $R_{11}$ and $R_{12}$ are the same or different, independently selected from H, $C_{1-4}$ alkyl, $C_{6-10}$ aryl that is unsubstituted or optionally substituted by one, two or more $R_a$; $R_a$ is as defined above. Preferably, $R_7$, $R_8$, $R_9$, $R_{10}$, $R_{11}$ and $R_{12}$ are the same or different, independently selected from H, methyl, phenyl, tolyl. Further preferably, $R_7$, $R_8$, $R_9$, $R_{10}$, $R_{11}$ and $R_{12}$ are the same or different, independently selected from H, methyl. Further preferably, $R_7$, $R_8$, $R_9$, $R_{10}$, $R_{11}$ and $R_{12}$ are the same, selected from H.

According to the present invention, $R_{13}$, $R_{16}$, $R_{17}$ and $R_{18}$ are the same or different, independently selected from H, $C_{1-4}$ alkyl, $C_{6-10}$ aryl that is unsubstituted or optionally substituted by one, two or more $R_a$; $R_a$ is as defined above. Preferably, $R_{13}$, $R_{16}$, $R_{17}$ and $R_{18}$ are the same or different, independently selected from H, methyl, phenyl, tolyl. Further preferably, $R_{13}$, $R_{16}$, $R_{17}$ and $R_{18}$ are the same or different, independently selected from H, methyl. Further preferably, $R_{13}$, $R_{16}$, $R_{17}$ and $R_{18}$ are the same, selected from H.

According to the present invention, a is an integer between 0-20,000, for example, a is 1, 50, 500, 1,000, 2,000, 3,000, 4,000, 5,000, 6,000, 7,000, 8,000, 9,000, 10,000, 12,000, 15,000, 18,000 or 20,000, such as a is an integer between 1-7,000; preferably, a is an integer between 50-3,000.

According to the present invention, b is an integer between 0-2,000, for example, 1, 5, 50, 100, 500, 1,000, 1,500 or 2,000; c is an integer between 0-2,000, for example, 1, 5, 50, 100, 500, 1,000, 1,500 or 2,000; d is an integer between 0-2,000, for example, 1, 5, 50, 100, 500, 1,000, 1,500 or 2,000; e is an integer between 0-20,000, such as 1, 50, 500, 1,000, 2,000, 3,000, 4,000, 5,000, 6,000, 7,000, 8,000, 9,000, 10,000, 12,000, 15,000, 18,000 or 20,000; f is an integer between 0-2,000, such as 1, 5, 50, 100, 500, 1,000, 1,500 or 2000.

According to the present invention, g is an integer between 1-10,000, for example, 1, 50, 500, 1,000, 2,000, 3,000, 4,000, 5,000, 6,000, 7,000, 8,000, 9,000 or 10,000.

According to the present invention, a' is an integer between 0-20,000, such as 1, 50, 500, 1,000, 2,000, 3,000, 4,000, 5,000, 6,000, 7,000, 8,000, 9,000, 10,000, 12,000, 15,000, 18,000 or 20,000; b' is an integer between 0-2,000, for example, 1, 5, 50, 100, 500, 1,000, 1,500 or 2,000; c' is an integer between 0-2,000, such as 1, 5, 50, 100, 500, 1,000, 1,500 or 2,000; d' is an integer between 0-2,000, such as 1, 5, 50, 100, 500, 1,000, 1,500, or 2,000; e' is an integer between 0-10,000, such as 1, 50, 500, 1,000, 2,000, 3,000, 4,000, 5,000, 6,000, 7,000, 8,000, 9,000, or 10,000; f' is an integer between 0-2,000, for example, 1, 5, 50, 100, 500, 1,000, 1,500, or 2,000. Preferably, a' and e' are not 0 at the same time.

According to the present invention, h is an integer between 0-2,000, for example, 1, 5, 50, 100, 500, 1,000, 1,500 or 2,000; i is an integer between 0-2,000, such as 1, 5, 50, 100, 500, 1,000, 1,500, or 2,000; j is an integer between 0-2,000, such as 1, 5, 50, 100, 500, 1,000, 1,500, or 2,000; k is an integer between 0 and 2,000, for example, 1, 5, 50, 100, 500, 1,000, 1,500, or 2,000.

According to the present invention, n' is an integer between 1-10, for example, 1, 2, 3, 4, 5, 6, 7, 8, 9, or 10. Preferably, n' is 1 or 2.

According to the present invention, the weight ratio of the polymer and iodine in the iodine complex is 1:0.00001-1.5, for example, 1:0.00001, 1:0.0001, 1:0.001, 1:0.005, 1:0.01, 1:0.05, 1:0.1, 1:0.2, 1:0.3, 1:0.4, 1:0.5, 1:0.6, 1:0.7, 1:0.8, 1:0.9, 1:1, 1:1.2 or 1:1.5.

The present invention also provides a preparation method of the iodine complex, the method comprises the following steps:
reacting the polymer comprising a structural unit represented by Formula (I) and optionally at least one of structural units represented by Formula (II), Formula (III) and Formula (IV) with iodine to prepare the iodine complex;
wherein, the reaction may be a gas-solid reaction, a solid-liquid reaction or a liquid-liquid homogeneous reaction;
the gas-solid reaction is a reaction by contacting an iodine-containing gas with the polymer solid comprising the structural unit represented by Formula (I) and optionally at least one of structural units represented by Formula (II), Formula (III) and Formula (IV);
the solid-liquid reaction is a reaction between an iodine-containing solution and a polymer solid comprising the structural unit represented by Formula (I) and optionally at least one of structural units represented by Formula (II), Formula (III) and Formula (IV);
the liquid-liquid homogeneous reaction is a homogeneous reaction after mixing an iodine-containing solution and a solution of the polymer comprising the structural unit represented by Formula (I) and optionally at least one of structural units represented by Formula (II), Formula (III) and Formula (IV).

According to the present invention, the person skilled in the art may make reasonable adjustments to the reaction temperature and the reaction time to prepare iodine complexes with different iodine contents; exemplarily, the temperature of the reaction is, for example, minus 20° C. to 110° C., the reaction time is 0.5-250 h.

According to the present invention, the reaction is carried out under hermetic conditions.

According to the present invention, the iodine-containing gas may be a gas obtained by the sublimation of solid elemental iodine; the iodine-containing solution may be an iodine-containing solution which is formed from solid elemental iodine or a substance containing polyiodide ion and a solvent; the solvent may be, for example, water, dimethyl sulfoxide, acetic acid, ethanol, etc.; the iodine-containing solid may be elemental iodine or a substance containing polyiodide ion; the solution of the polymer comprising the structural unit represented by Formula (I) and optionally at least one of structural units represented by Formula (II), Formula (III) and Formula (IV) may be a solution that formed from the polymer solid comprising the structural unit represented by Formula (I) and optionally at least one of structural units represented by Formula (II), Formula (III) and Formula (IV) and an organic solvent; the organic solvent may be, for example, dimethyl sulfoxide, acetic acid, ethanol, etc.

According to the present invention, the polymer containing the structural unit represented by Formula (I) can be prepared by the following method:
(i) an epoxidized polymer is prepared by oxidation reaction of a polymer containing the structural unit represented by Formula (V),

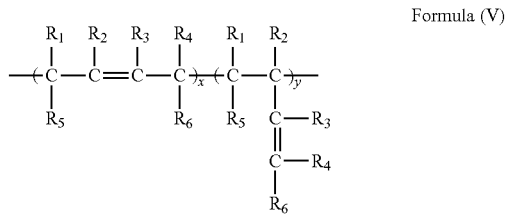

Formula (V)

in Formula (V), x=a+b+c, y=d+e+f; $R_1$, $R_2$, $R_3$, $R_4$, $R_5$, $R_6$, a, b, c, d, e and f are as defined above;

(ii) the polymer products are obtained by hydrolysis of the epoxidized polymer, or by hydrolysis first and then catalytic hydrogenation; or by catalytic hydrogenation first and then hydrolysis.

According to the present invention, the polymer containing the structural unit represented by Formula (V) may also contain at least one of the structural units represented by Formula (II), Formula (VI) and Formula (VII):

Formula (II)

in Formula (II), $R_{19}$ and g are as defined above;

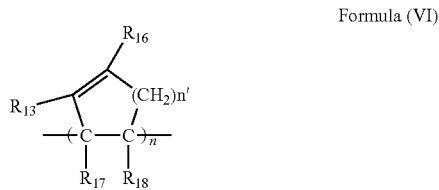

Formula (VI)

in Formula (VI), n=h+i+j+k, $R_{13}$, $R_{16}$, $R_{17}$, $R_{18}$, h, i, j, k and n' are as defined above;

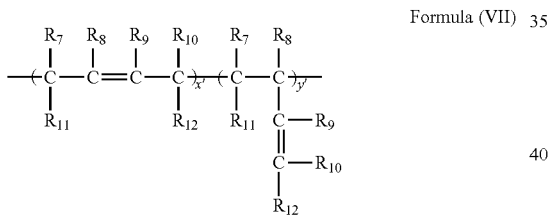

Formula (VII)

in Formula (VII), x'=a'+b'+c', y'=d'+e'+f'; $R_7$, $R_8$, $R_9$, $R_{10}$, $R_{11}$, $R_{12}$, a', b', c', d', e' and f' are as defined above.

According to the present invention, in step (i), the polymer containing the structural unit represented by Formula (V) may be obtained by polymerization of a conjugated diene monomer, the conjugated diene monomer can be, for example, 1,3-butadiene, 1,3-pentadiene or isoprene.

In step (i), the polymer containing the structural units represented by Formula (V) and at least one of Formula (II) and/or Formula (VI) is obtained by copolymerization of a conjugated diene monomer and at least one of monomers with a structure represented by $R_{19}$—CH=CH$_2$ and/or

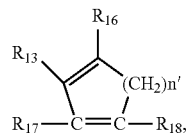

the conjugated diene monomer may be, for example, 1,3-butadiene, 1,3-pentadiene or isoprene, $R_{19}$, $R_{13}$, $R_{16}$, $R_{17}$, $R_{18}$ and n' are as defined above.

In step (i), the polymer containing the structural unit represented by Formula (V) and at least one of the structural units represented by Formula (VII) is obtained by the copolymerization of at least two conjugated diene monomers, the conjugated diene monomer may be, for example, 1,3-butadiene, 1,3-pentadiene or isoprene.

In step (i), the polymer containing the structural unit represented by Formula (V), at least one of the structural units represented by Formula (VII) and at least one of the structural units represented by Formula (II) and/or Formula (VI) is obtained by the copolymerization of at least two conjugated diene monomers and at least one of monomers with a structure represented by $R_{19}$—CH=CH$_2$ and/or

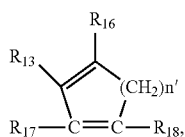

the conjugated diene monomer may be, for example, 1,3-butadiene, 1,3-pentadiene or isoprene, $R_{19}$, $R_{13}$, $R_{16}$, $R_{17}$, $R_{18}$ and n' are as defined above.

Specifically, the preparation method of the polymer containing the structural unit represented by Formula (V) is as follows:

a continuous solution polymerization method is used: a conjugated diene (such as 1,3-butadiene, 1,3-pentadiene, or isoprene) is mixed with alkane, aromatic hydrocarbon or a mixture of the both (such as toluene-heptane mixture) as solvent, and an initiator (such as nickel naphthenate-BF$_3$-Et$_3$Al) is added to initiate the reaction, a molecular weight regulators (such as octanol and other alcohols) is optionally added to adjust the molecular weight, a reaction terminator (such as ethanol, etc.) to terminate the reaction, and the polymer containing the structural unit represented by Formula (V) is prepared.

According to the present invention, in step (i), the oxidation reaction comprises, but is not limited to, chlorohydrin method, peroxide epoxidation method or direct oxygen oxidation method. The oxidation reaction is an epoxidation reaction, and the oxidation reaction may be a partial epoxidation or a complete epoxidation.

Exemplarily, the peroxide may be selected from one or a mixture of hydrogen peroxide, peroxyformic acid, peroxyacetic acid, peroxybenzoic acid, m-chloroperoxybenzoic acid, tert-butyl hydroperoxide and the like.

Exemplarily, the oxidation reaction may be carried out in an organic solvent containing the polymer, or also in a water/organic solvent emulsion; the organic solvent comprises, but is not limited to, aliphatic alkanes, halogenated aliphatic hydrocarbons, aromatic hydrocarbons, cycloalkanes, mineral spirits, etc., preferably hexane, cyclohexane, heptane, methylene chloride, benzene, toluene, mineral spirits, etc. The temperature of the oxidation reaction is 0-120° C., preferably 20-80° C.

According to the present invention, in step (ii), the catalytic hydrogenation can open the epoxy ring of the epoxidized polymer by catalytic hydrogenation and the like, to obtain the polymer containing hydroxyl groups on the C—C chain; the hydrolysis may include hydrolyzing the epoxidized polymer with conventional acidic or alkaline substances to open the epoxy ring, so as to obtain a polymer containing adjacent dihydroxyl groups on the C—C chain.

The catalytic hydrogenation can be a partial catalytic hydrogenation or a complete catalytic hydrogenation, the hydrolysis may be partial hydrolysis or a complete hydrolysis. The specific reaction conditions and material ratios in the catalytic hydrogenation and hydrolysis herein are all conventional selections in the field, to which no special restrictions are applied, as long as the polymer with the structural unit represented by Formula (I) of the present application can be prepared.

Exemplarily, the acidic substances comprise inorganic acids such as aqueous hydrogen halide, sulfuric acid, and nitric acid, etc.; organic acids such as alkyl sulfonic acids, etc.; solid acids; heteropoly acids, etc.

Exemplarily, the alkaline substances comprise aqueous solutions of hydroxides and carbonates of alkali metals.

Exemplarily, the catalytic hydrogenation is carried out under the catalysis of Raney nickel, triphenylphosphine rhodium chloride, or platinum, palladium, etc.

Exemplarily, the catalytic hydrogenation reaction can be carried out in an organic solvent containing the polymer, or also in a water/organic solvent emulsion; the organic solvent comprises, but is not limited to, aliphatic alkanes, halogenated aliphatic hydrocarbons, cycloalkanes, mineral spirits, cyclic ether compounds, alcohols, etc., preferably selected from hexane, cyclohexane, tetrahydrofuran, methanol, ethanol, etc. The temperature of the catalytic hydrogenation reaction is 0 to 120° C., preferably 20 to 80° C.

Exemplarily, the hydrolysis reaction can be carried out in an organic solvent containing the polymer, or also in a water/organic solvent emulsion; the organic solvents comprise, but are not limited to, aliphatic alkanes, halogenated aliphatic hydrocarbons, aromatic hydrocarbons, cycloalkanes, mineral spirits, cyclic ether compounds, sulfoxides, sulfones, pyrrolidone, methylpyrrolidone, etc., preferably tetrahydrofuran, dimethyl sulfoxide, methylpyrrolidone etc. The temperature of the hydrolysis reaction is from –20° C. to 150° C., preferably from –10° C. to 80° C.

The present invention also provides use of the above-mentioned iodine complex as a radiation marker, or in an iodine therapeutic agent, or in a polarizing film.

Preferably, the radiation marker is a radiopaque marker.

Terms and Explanations

The term "$C_{1-12}$ alkyl" should be interpreted as preferably representing a linear or branched saturated monovalent hydrocarbon group having 1-12 carbon atoms, preferably $C_{1-8}$ alkyl. "$C_{1-8}$ alkyl" should be interpreted as preferably representing a linear or branched saturated monovalent hydrocarbon group which having 1, 2, 3, 4, 5, 6, 7 or 8 carbon atoms. The alkyl group is, for example, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethyl-propyl, 4-methylpentyl, 3-methylpentyl, 2-methylpentyl, 1-methylpentyl, 2-ethylbutyl, 1-ethylbutyl, 3,3-dimethyl-butyl, 2,2-dimethylbutyl, 1,1-dimethylbutyl, 2,3-dimethyl-butyl, 1,3-dimethylbutyl or 1,2-dimethylbutyl, etc. or their isomers. Particularly, the group has 1, 2, 3, 4, 5 or 6 carbon atoms ("$C_{1-6}$ alkyl"), such as methyl, ethyl, propyl, butyl, isopropyl, isobutyl, sec-butyl, tert-butyl; more specifically, the group has 1, 2 or 3 carbon atoms ("$C_{1-3}$ alkyl"), such as methyl, ethyl, n-propyl or isopropyl.

The term "$C_{6-20}$ aryl" should be interpreted as preferably representing a monovalent aromatic or partially aromatic monocyclic, bicyclic or tricyclic hydrocarbon ring having 6-20 carbon atoms, preferably a "$C_{6-14}$ aryl". The term "$C_{6-14}$ aryl" should be interpreted as preferably representing a monovalent aromatic or partially aromatic monocyclic, bicyclic or tricyclic hydrocarbon ring having 6, 7, 8, 9, 10, 11, 12, 13, or 14 carbon atoms ("$C_{6-14}$ aryl"), especially the ring having 6 carbon atoms ("$C_6$ aryl"), such as phenyl; or biphenyl, or a ring having 9 carbon atoms ("$C_9$ aryl"), such as indanyl or indenyl, or a ring having 10 carbon atoms ("$C_{10}$ aryl"), such as tetrahydronaphthyl, dihydronaphthyl or naphthyl, or a ring having 13 carbon atoms ("$C_{13}$ aryl"), such as fluorenyl, or a ring having 14 carbon atoms ("$C_{14}$ aryl"), such as anthryl.

The Beneficial Effects of the Present Invention

The present invention provides an iodine complex and its preparation method thereof, and its use as a radiation marker, in an iodine therapeutic agent or in a polarizing film. The iodine complex is formed by the complexation of a polymer carrier and iodine; on the one hand the polymer carrier has good biocompatibility, on the other hand the iodine complex has a low iodine dissolution rate and can be used as a radiation marker, or for the preparation of iodine therapeutics, or for the preparation of polarizing film. Furthermore, the content of iodine in the iodine complex can be adjusted as required based on the preparation method provided by the present invention, and the iodine content is adjustable within 0.001-60%. The difference in iodine contents can affect the iodine complex transmission clarity as a radiation marker and the amount of iodine therapeutic agent.

DETAILED DESCRIPTION OF THE INVENTION

Figure 1:
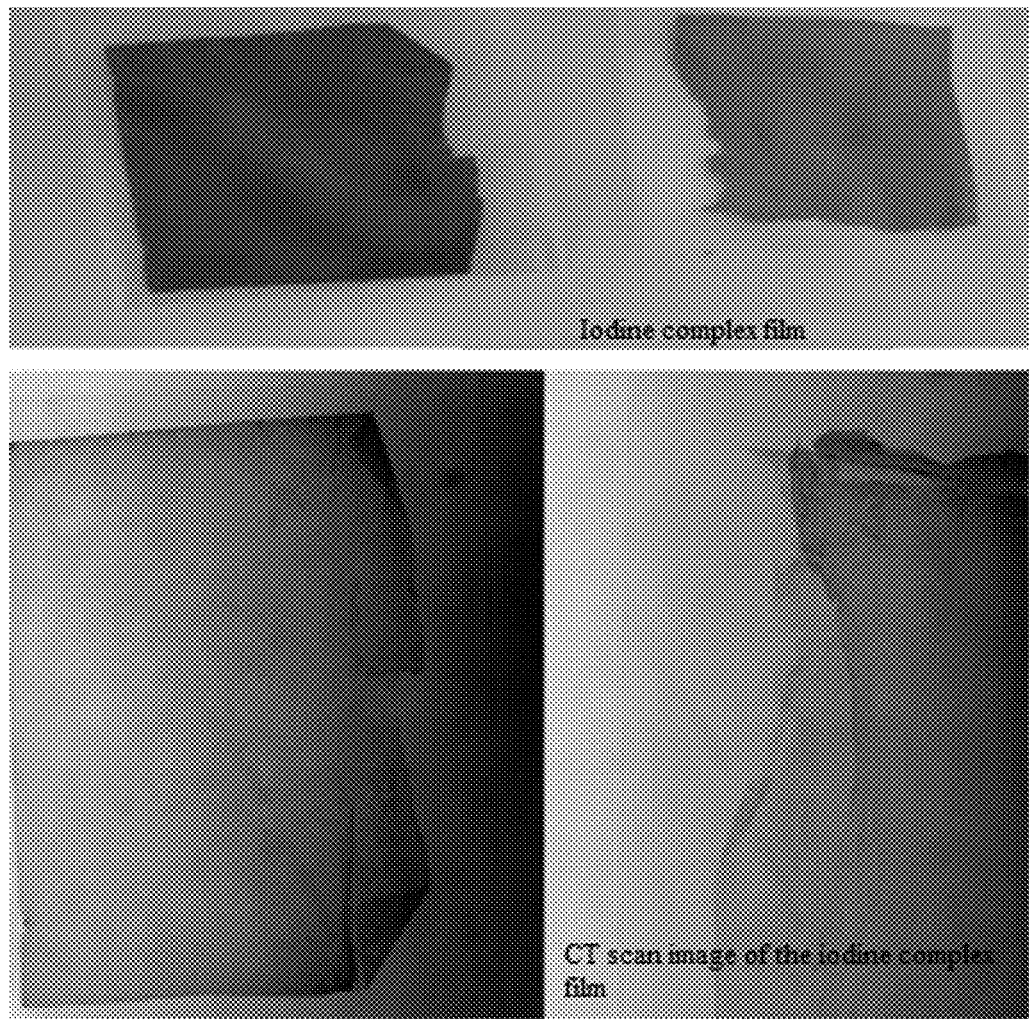
FIG. 1 is an industrial CT scan image of the iodine complex film of Example 5.

The present invention will be further illustrated with reference to the specific examples below. It should be understood that these examples below are only used to exemplify the present invention, but are not intended to limit the scope of the present invention. Any technique achieved basing on the above contents of the invention also fall within the scope intended to be protected by the present invention.

Unless otherwise specified, the experimental methods used in the following examples are conventional methods; unless otherwise specified, the reagents and materials used in the following examples can be obtained from commercial sources.

Instruments and Equipments

Material structure test $^1$HNMR and $^{13}$CNMR is carried out on JOEL's 600M pulse Fourier transform nuclear magnetic resonance spectrometer;

IR is tested on Thermofisher's Fourier Transform Infrared Spectrometer Nicolet IS50;

Tg value is tested on Q100 Differential Scanning Calorimeter, TA Company;

TGA is tested on Q500 thermogravimetric analyzer, TA company;

The molecular weight of the polymer is tested on Agilent's PL-GPC50 (with a refractive index detector and an evaporative light scattering detector);

The degree of polarization is tested on an ultraviolet-visible spectrophotometer UV3600 (Shimadzu Corporation, Japan).

Preparation Example 1 cis-Polybutadiene: commercially available polybutadiene mass (purchased from Sichuan Petrochemical Ltd., 1,4-cis content ≥98%, and 2% 1,4-trans and the structure represented by Formula IV; the number average molecular weight $\overline{M}_n$=170,000) are cut into approximately 2 mm mass particles.

Epoxidation: Into a 250 ml three-neck flask equipped with a stirrer and a thermometer, 7 g of the above cis-polybutadiene mass particles and 100 ml of methylene chloride was added, the mass was dissolved and stirred under constant temperature in water bath at room temperature. Nitrogen gas was introduced for a few minutes when the mass was completely dissolved and became a sticky state. 9.90 g formic acid was added; 21.40 g 30% aqueous hydrogen peroxide solution was added dropwise with stirring; the reaction temperature was held for about 15 hours; according to $^1$HNMR (CDCl$_3$) analysis, the characteristic chemical shift peaks of 1,4-cis double bond disappeared (the characteristic chemical shift of the epoxy group δ=2.98, the characteristic chemical shift of 1,4-cis double bond δ=5.40). The reaction product is neutralized with 10% sodium carbonate solution to pH=7, the water phase was separated, the organic phase was washed and the phases were separated; absolute ethanol was added into the separated gel to precipitate, the precipitate was separated and washed with absolute ethanol once, waste liquid was filtered out to obtain a wet mass, which was dried at room temperature for 12 hours, and then dried in a vacuum oven at 40° C. for about 24 hours to constant weight to obtain 7.3 g of epoxidized butadiene rubber.

Hydrolysis: 1 g of the epoxidized butadiene rubber prepared above was weighted and dissolved in 100 ml of tetrahydrofuran, into which a solution of 5 ml water and 1 ml perchloric acid was added dropwise with stirring at 25° C. The addition was completed in 30 min and the stirring was continued at 25° C. for 12 hours. According to $^1$HNMR (DMSO) analysis, the characteristic chemical shift peaks of the epoxidized butadiene rubber had disappeared (the characteristic chemical shift of the epoxy group, δ=2.98, the characteristic chemical shift of the adjacence dihydroxyls, δ=4.18). Sodium carbonate was added into the reaction solution for neutralization. 1000 ml of water was added into the reaction solution dropwise to precipitate; the precipitate was separated, into which 400 ml water was added and then soaked for 24 hours. The water was filtered out. The resulting polymer substance was dried for 24 hours at room temperature and then at 40° C. in a vacuum oven to constant weight. 1.12 g of solid matter was obtained. The molecular weight of the product was $\overline{M}n$=146,000, the molar content of adjacent dihydroxyl C4 units was 98%, its Tg value was 56° C.

Preparation Example 2

2 g of the epoxidized butadiene rubber prepared as above was taken and dissolved in 200 ml of freshly distilled tetrahydrofuran, and then was added into a 500 ml stainless steel autoclave; 0.4 g Raney nickel (covered by ethanol, rinsed with tetrahydrofuran 3 times before being added into the reactor) was added. The autoclave was filled with nitrogen gas to a pressure of 1 MPa, then released to normal pressure; the nitrogen gas filling and pressure releasing were repeated 3 times. Hydrogen was introduced with stirring at 50° C. and pressurized to 1 MPa. The hydrogen pressure was held, and the reaction was carried out under stirring for 12 hours. $^1$HNMR test was carried out, and the degree of epoxy group opening was about 75% (mol).

The reaction liquid was cooled to 0° C., and the pressure is released. The catalyst was filtered out. Into the reaction liquid without the catalyst, a solution formulated with 5 ml of water, 1 ml of perchloric acid, 5 ml of tetrahydrofuran was added dropwise within 30 mins; the reaction temperature was allowed to rise to 25° C., the temperature was held for 12 hours under stirring. According to $^1$HNMR (DMSO) analysis, the characteristic chemical shift peaks of epoxidized butadiene rubber disappeared. 0.37 g of solid sodium carbonate was added into the reaction solution and stirred for 2 hours. Water was added dropwise into the reaction solution, and precipitate the precipitate; water was added for soaking 24 hours, then water was filtered out. The obtained polymer material was dried at room temperature for 24 hours, then dried to constant weight in a vacuum oven at 40° C. 2.35 g of milky white solid matter was obtained. Number average molecular weight is 133,000, the molar content of adjacent dihydroxyl C4 units is 24.7%, Tg value is 66° C.

Preparation Example 3

Styrene butadiene rubber: commercially available styrene butadiene rubber mass (Qilu Petrochemical Co., Ltd., styrene unit/butadiene unit (S/B): 27/73, weight average molecular weight $\overline{M}_w$=320,000) was cut into approximately 2 mm rubber particles.

Epoxidation: into a 1000 ml three-neck flask equipped with a stirrer and a thermometer, 6 g of the above styrene butadiene rubber mass particles and 550 ml of toluene was added. The particles were dissolved and stirred under constant temperature in water bath at room temperature. Nitrogen was introduced for a few minutes when the mass was completely dissolved and became a sticky state. The mixture was heated to 40° C. and 3.0 g of formic acid was added, 8.2 g of 30% aqueous hydrogen peroxide solution was added dropwise with stirring; the reaction temperature was held for about 5 hours. According to $^1$HNMR (CDCl$_3$) analysis, the characteristic chemical shift peak of double bonds disappeared. The reaction product is neutralized with 10% sodium carbonate solution to pH=7; the water phase was separated. The remaining phase was washed and the liquid phases were separated. Absolute ethanol was added into the separated gel to precipitate; the precipitate was analyzed, which was washed with absolute ethanol once; waste liquid was filtered out to obtain wet gel, which was dried at room temperature for 12 h, and then in a vacuum oven at 40° C. for about 24 hours to constant weight. 6.33 g of epoxidized styrene butadiene rubber was obtained.

Hydrolysis: 1 g of the epoxidized styrene butadiene rubber as prepared above was taken and dissolved in 100 ml of tetrahydrofuran. A solution formulated with 5 ml of water and 1 ml of perchloric acid was added dropwise with stirring at 25° C. The addition was completed in 30 min and the stirring was continued at 25° C. for 12 hours. According to $^1$HNMR (DMSO) analysis, the epoxy characteristic chemical shift peak disappeared. Sodium carbonate was added into the reaction solution for neutralization. 1000 ml water was added into the reaction solution dropwise to precipitate; the precipitate was separated, into which 500 ml water was added and soaked for 24 hours. Water was filtered out. The resulting polymer substance was dried for 24 hours at room temperature and at 40° C. in a vacuum oven to constant weight. 1.1 g white solid material was obtained, the proportion of adjacent dihydroxyl C4 units was found to be 62%.

Example 1

1 g of translucent solids prepared according to the method of Preparation Example 1 and 1.1 g of elemental iodine particles were added together into a 20 ml glass flask, which was then sealed and stored at 50° C. for 24 hours, an iodine complex was obtained by gas-solid reaction. The iodine complex is black hard lumps with a weight of 2.0 g; a mass percentage of iodine in the iodine complex is 50%.

Example 2

1 g of translucent solids prepared according to the method of Preparation Example 1 was dissolved in 20 ml dimethyl sulfoxide to form a dimethyl sulfoxide solution of the polymer; 1.1 g of elemental iodine particles was added at 25° C. and stirred, and the reaction liquid slowly turns brown due to the dissolution of iodine. After 2 hours, stirring was stopped, and the liquid-liquid homogeneous reaction completed. 200 ml of methanol was added, and a dark brown solid sticky mass precipitate. Such solid was dried under vacuum at 30° C. for 24 hours, and then 1.48 g black solid lump, which was the iodine complex of the present invention, the weight percentage of iodine in the iodine complex was 32%.

Example 3

1 g of the translucent solid prepared by the method of Preparation Example 1 was added into a sealed glass bottle, then 20 ml of water and 2.0 g of elemental iodine were added, the elemental iodine dissolved in water was absorbed by the solid (that is, the liquid-solid reaction). The mixture was stirred at 25° C. for 8 hours; solid matter without dissolution and deformation was black. The solid material was taken out and dried under vacuum at 30° C. for 24 hours, and the weight was 1.21 g, which was the iodine complex of the present invention, the weight percentage of iodine in the iodine complex was 17.4%.

Example 4

Adsorption of Elemental Iodine Experiment:

Related substances: the solid products (particles with a size of about 3 mm) prepared according to the methods of Preparation Examples 1, 2 and 3, ethylene-vinyl alcohol polymer (EVOH, F171B, Kuraray Company, Japan, ethylene content 32%, particles with a size of about 3 mm), polyvinyl alcohol (PVA, Shanghai Chenqi Chemical Technology Co., Ltd., degree of polymerization of 1,680, degree of alcoholysis of 99%, molecular weight of 81,000, white powder), soluble starch of analytical pure grade were baked at 120° C. to constant weight before use.

2 g (accuracy: 0.0001 g) of the above 6 kinds of solids was taken and put into 100 ml glass bottles, respectively. Then open vials containing 4 g (accuracy 0.0001 g) of elemental iodine were put into the above glass bottles, respectively, which were sealed and stood at 20° C. for 100 hours. The the solid materials were taken out and weighted to calculate the weight gain.

| Substance | Weight Gain (g) | Weight gain ratio (%)[a] | Mass percentage of iodine (%) |
|---|---|---|---|
| Preparation Example 1 | 2.8 | 140 | 58 |
| Preparation Example 2 | 0.58 | 29 | 22.5 |
| Preparation Example 3 | 1.7 | 85 | 46.0 |
| EVOH | 0.01 | 0.5 | 0.5 |
| PVA | 0.05 | 2.5 | 2.4 |
| Soluble starch | 0.48 | 24 | 19.4 |

[a] weight gain ratio = weight gain / weight of solid matter before absorbing iodine x 100%

Example 5

1 g of the translucent solid obtained in Preparation Example 1 was dissolved in 20 ml of dimethyl sulfoxide, and the obtained solution is poured into a stainless steel tray (304 materials, 27×20×2 cm) to level naturally, and then was dried to constant weight to obtain a soft polymer film. The polymer film and iodine pellets were placed in a closed glass container under 50° C. for 12 hours, 1.2 g black complex film was obtained. The mass percentage of iodine in the iodine complex was 16.7%.

The iodine complex film obtained in Example 5 was scanned and imaged on XTH225 series industrial CT equipped with a 225 kV microfocus X-ray source. The results are shown in FIG. 1.

As can be seen from analysis of the IR analysis spectrum, as compared with the translucent solid prepared in Preparation Example 1, the peak of the stretching vibration of the hydroxyl groups of the iodine complex obtained in Example 5 gradually shifts to the direction of high wave number, which is the so-called blue shift, indicating the weakening of the hydroxyl hydrogen bond in the polymer structure, the lone pairs of electrons provided by the oxygen atoms in the two pairs of adjacent hydroxyl groups enter into the vacant valence electron orbital provided by iodine, form the iodine complex by way of coordination bond.

Figure 2:
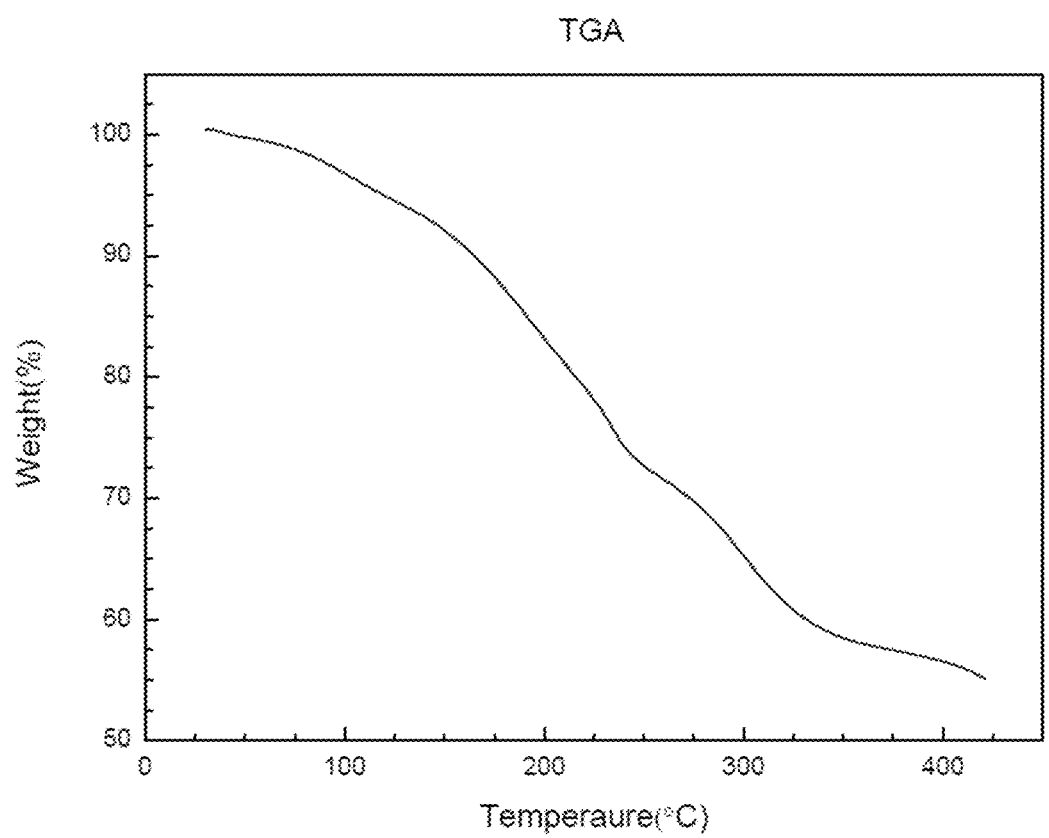
FIG. 2 is a TGA diagram of the iodine complex of Example 5.

The iodine complex obtained in Example 5 was subjected to weight loss analysis. As shown in FIG. 2, as the temperature increasing, the iodine constantly dissociated and volatilized, and iodine volatilized completely at 350° C.

Example 6

For saline immersion test, the following materials were prepared:
  the iodine complex as prepared in Example 1 (iodine content: 50.0%);
  the starch bound with iodine as prepared in Example 4 (iodine content: 19.4%);
  commercial povidone iodine solid (iodine content: 11.2%);
  physiological saline prepared according to the standard method in Chinese Pharmacopoeia.

1 g of the above substances were weighted accurately, and added into 100 ml physiological saline and soaked for 24 hours. The solid material was taken out, rinsed with a small amount of physiological saline, and the rinse liquid was combined with the soaking solution. The soaking liquid was titrated by using a sodium thiosulfate standard solution to calculate the iodine dissolution rate.

Iodine dissolution rate %=(iodine content in soaking solution in wt %×soaking solution weight)/ Weight of iodine before soaking solids×100.

| Substance | Iodine wt % | Soaked state | Iodine dissolution rate (wt %) |
|---|---|---|---|
| Example 1 | 50.0 | No shape change of solid | 0.24 |
| Povidone iodine | 11.2 | Dissolved | 100 |
| Starch iodine complex | 19.4 | Dissolved | 100 |

Example 7

The iodine-containing film prepared in Example 5 is cut into a 5 cm×4 cm piece with a thickness of 0.05-0.07 mm; then the piece was stretched on a stretching machine into a film with a thickness of 0.02 mm. The stretched iodine film was cut into two pieces of 2 cm×2 cm size, which were each loaded on a blank glass sheet (100% light transmittance). The transmittance Tsp (monomer transmittance, theoretical value is 50%), T⊥ (the orthogonal transmittance measured when the absorption axis of two polarizing films is placed vertically), T∥ (Parallel transmittance measured when the absorption axis of two polarizing films are placed in parallel) of the film were measured with an ultraviolet-visible spectrophotometer, and polarization degree of the film PE=(T∥−T⊥)/(T∥+T⊥)×100% was calculated. After testing and calculation, the degree of polarization is PE=90%. Referring to Example 6, the stretched iodine film was tested, it found that the iodine film soaked in physiological saline will not deform, and its iodine dissolution rate is 0.09 wt %; as compared with PVA with higher water solubility, the polarizing film prepared by the polymer provided by the present invention had better moisture resistance than the PVA polarizing film.

The embodiments of the present invention have been described above. However, this invention is not limited to the above embodiments. Any modification, equivalent replacements, or improvements made within the spirit and principle of the present invention shall be included in the protection scope of the present invention.

The invention claimed is:

1. An iodine complex obtained by complexing with iodine a polymer containing a structural unit represented by Formula (I) and optionally at least one of structural units represented by Formula (II), Formula (III) and Formula (IV):

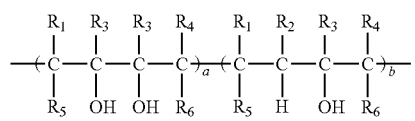

Formula (I)

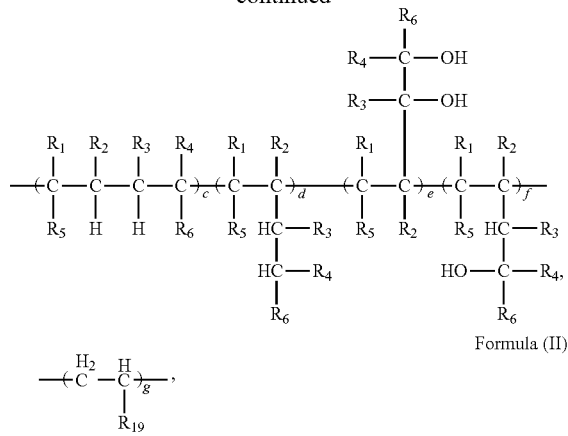

Formula (II)

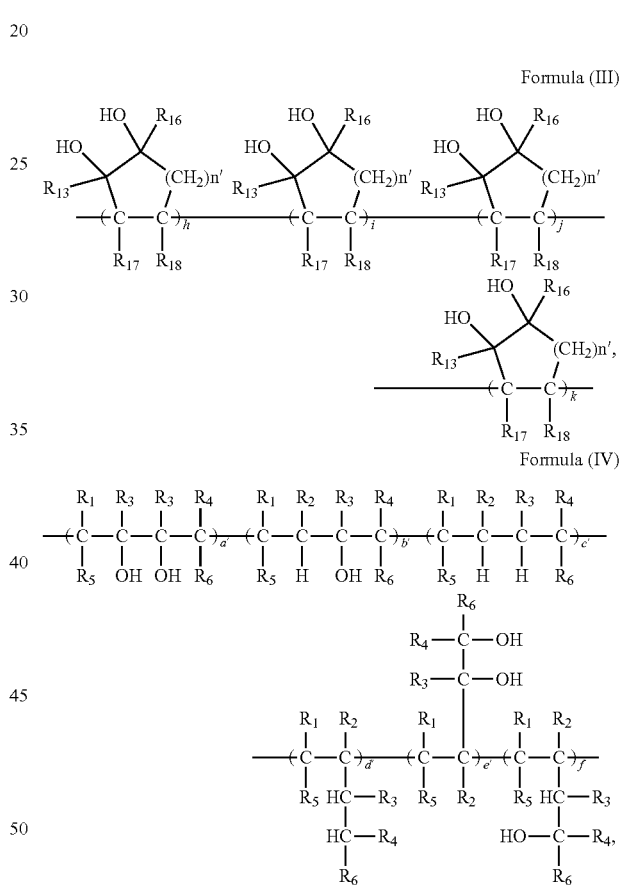

in Formula (I), $R_1$, $R_2$, $R_3$, $R_4$, $R_5$ and $R_6$ are the same or different, independently selected from H, $C_{1-8}$ alkyl, and $C_{6-20}$ aryl that is unsubstituted or substituted by one, two or more $R_a$; each $R_a$ is the same or different, independently selected from $C_{1-12}$ alkyl;

a is an integer greater than or equal to 50, e is an integer greater than or equal to 1, b, c, d, and f are independently integers greater than or equal to 0;

in Formula (II), $R_{19}$ is selected from H, cyano, $C_{1-8}$ alkyl, substituted and unsubstituted $C_{3-10}$ cycloalkyl, and substituted and unsubstituted $C_{6-20}$ aryl, wherein the substituents are one, two or more $R_a$, each $R_a$ being the same or different, independently selected from $C_{1-12}$ alkyl; and g is an integer greater than or equal to 1;

in Formula (III), $R_{13}$, $R_{16}$, $R_{17}$ and $R_{18}$ are the same or different, independently selected from H, $C_{1-8}$ alkyl, and $C_{6-20}$ aryl that is unsubstituted or substituted by one, two or more $R_a$, each $R_a$ being the same or different, independently selected from $C_{1-12}$ alkyl; and h, I, j, k and n' are independently integers greater than or equal to 1; and in Formula (IV), $R_7$, $R_8$, $R_9$, $R_{10}$, $R_{11}$ and $R_{12}$ are the same or different, independently selected from H, $C_{1-8}$ alkyl, and $C_{6-20}$ aryl that is unsubstituted or substituted by one, two or more $R_a$, each $R_a$ being the same or different, independently selected from $C_{1-12}$ alkyl; and a', b', c', d', e' and f' are independently integers greater than or equal to 0, and are not 0 at the same time.

2. The iodine complex according to claim 1, wherein $R_1$, $R_2$, $R_3$, $R_4$, $R_5$ and $R_6$ are the same or different, independently selected from H, $C_{1-4}$ alkyl, and $C_{6-10}$ aryl that is unsubstituted or substituted by one, two or more $R_a$.

3. The iodine complex according to claim 1, wherein $R_{19}$ is selected from H, cyano, $C_{1-4}$ alkyl, and $C_{6-10}$ aryl that is unsubstituted or substituted by one, two or more $R_a$.

4. The iodine complex according to claim 3, wherein $R_7$, $R_8$, $R_9$, $R_{10}$, $R_{11}$ and $R_{12}$ are the same or different, independently selected from H, $C_{1-4}$ alkyl, and $C_{6-10}$ aryl that is unsubstituted or substituted by one, two or more $R_a$.

5. The iodine complex according to claim 1, wherein the iodine is selected from an iodine molecule, a polyiodide formed by binding an iodine molecule with iodide ion, and a mixture thereof.

6. A preparation method of the iodine complex according to claim 1, comprising:
reacting the polymer comprising the structural unit represented by Formula (I) and optionally at least one of structural units represented by Formula (II), Formula (III) and Formula (IV) carrying the iodine to prepare the iodine complex in a gas-solid reaction, a solid-liquid reaction or a liquid-liquid homogeneous reaction, wherein:
the gas-solid reaction is carried out by contacting an iodine-containing gas with a polymer solid comprising the structural unit represented by Formula (I) and at least one of structural units represented by Formula (II), Formula (III) and Formula (IV);
the solid-liquid reaction is carried out between an iodine-containing solution and a polymer solid comprising the structural unit represented by Formula (I) and at least one of structural units represented by Formula (II), Formula (III) and Formula (IV); and
the liquid-liquid homogeneous reaction is carried out by mixing an iodine-containing solution and a solution of the polymer comprising the structural unit represented by Formula (I) and at least one of structural units represented by Formula (II), Formula (III) and Formula (IV).

7. The preparation method according to claim 6, wherein
the polymer containing the structural unit represented by Formula (I) is prepared by a method comprising:
(i) preparing an epoxidized polymer by oxidation reaction of a polymer containing the structural unit represented by Formula (V),

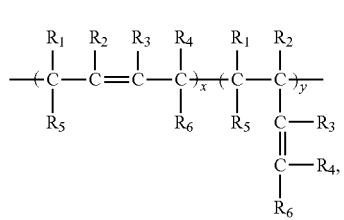

Formula (V)

wherein, in Formula (V), x=a+b+c, and y=d+e+f; and
(ii) obtaining the polymer containing the structural unit represented by Formula (I) by hydrolysis of the epoxidized polymer, or by hydrolysis first and then catalytic hydrogenation; or by catalytic hydrogenation first and then hydrolysis.

8. The preparation method according to claim 6, wherein the polymer comprising the structural unit represented by Formula (V) further comprises at least one of the structural units represented by Formula (II), Formula (VI) and Formula (VII),
wherein,

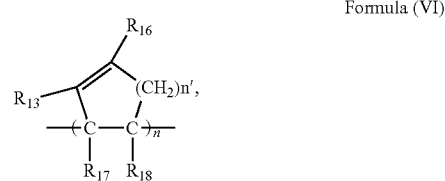

Formula (VI)

in Formula (VI), n=h+i+j+k; and

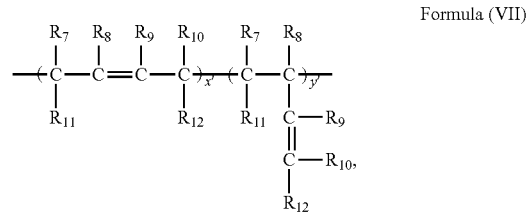

Formula (VII)

in Formula (VII), x'=a'+b'+c', and y'=d'+e'+f'.

9. The iodine complex according to claim 1, wherein $R_1$, $R_2$, $R_3$, $R_4$, $R_5$ and $R_6$ are the same or different, independently selected from H, methyl, phenyl, and tolyl.

10. The iodine complex according to claim 1, wherein a is an integer between 50-20,000, b is an integer between 0-2,000, c is an integer between 0-2,000, d is an integer between 0-2,000, e is an integer between 1-20,000, and f is an integer between 0-2,000.

11. The iodine complex according to claim 1, wherein a is an integer between 50-3,000.

12. The iodine complex according to claim 1, wherein $R_{19}$ is selected from phenyl, tolyl, and cyano, and g is an integer between 0-10,000.

13. The iodine complex according to claim 1, wherein a' is an integer between 0-20,000, b' is an integer between 0-2,000, c' is an integer between 0-2,000, d' is an integer between 0-2,000, e' is an integer between 0-10,000, and f' is an integer between 0-2,000.

14. The iodine complex according to claim 1, wherein a' and e' are not 0 at the same time; and/or, $R_7$, $R_8$, $R_9$, $R_{10}$, $R_{11}$ and $R_{12}$ are the same or different, independently selected from H, methyl, phenyl, and tolyl.

15. The iodine complex according to claim 1, wherein $R_{13}$, $R_{16}$, $R_{17}$ and $R_{18}$ are the same or different, independently selected from H, $C_{1-4}$ alkyl, and $C_{6-10}$ aryl that is unsubstituted or substituted by one, two or more $R_a$; h is an integer between 0-2,000, i is an integer between 0-2,000, j is an integer between 0-2,000, and k is an integer between 0 and 2,000.

16. The iodine complex according to claim 1, wherein $R_{13}$, $R_{16}$, $R_{17}$ and $R_{18}$ are the same or different, independently selected from H, methyl, phenyl, and tolyl;

and/or, n' is an integer between 1-10.

17. The iodine complex according to claim 1, wherein the polymer is a homopolymer, a random copolymer, or a block copolymer, and a weight ratio of the polymer and iodine in the iodine complex is 1:0.00001-1.5.

18. A radiation marker comprising the iodine complex according to claim 1.

19. An iodine therapeutic agent comprising the iodine complex according to claim 1.

20. A polarizing film comprising the iodine complex according to claim 1.

\* \* \* \* \*